(12) United States Patent
Niunoya et al.

(10) Patent No.: US 10,182,967 B2
(45) Date of Patent: Jan. 22, 2019

(54) PLUG AND BODILY FLUID-COLLECTING INSTRUMENT SET

(75) Inventors: Masatoshi Niunoya, Shunan (JP);
Ryusuke Okamoto, Shunan (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 942 days.

(21) Appl. No.: 13/502,479

(22) PCT Filed: Jan. 27, 2011

(86) PCT No.: PCT/JP2011/051604
§ 371 (c)(1),
(2), (4) Date: Apr. 17, 2012

(87) PCT Pub. No.: WO2011/093382
PCT Pub. Date: Aug. 4, 2011

(65) Prior Publication Data
US 2012/0203138 A1    Aug. 9, 2012

(30) Foreign Application Priority Data

Feb. 1, 2010  (JP) ................................ 2010-020382

(51) Int. Cl.
*A61B 5/15*    (2006.01)
*B65D 41/02*   (2006.01)
(Continued)

(52) U.S. Cl.
CPC ......... *A61J 1/1406* (2013.01); *A61B 5/15003* (2013.01); *A61B 5/154* (2013.01);
(Continued)

(58) Field of Classification Search
CPC ............ A61B 5/150015; A61B 5/1405; A61B 5/150259; B01L 3/50825; B65D 51/002
See application file for complete search history.

(56) References Cited

U.S. PATENT DOCUMENTS 3,954,614 A * 5/1976 Wright ................. B01L 3/5021
                                                    210/136
4,624,393 A   11/1986 Lopez
(Continued)

FOREIGN PATENT DOCUMENTS

EP    0 161 767 A2   11/1985
EP    0 829 250 A2    3/1998
(Continued)

OTHER PUBLICATIONS

International Preliminary Report on Patentability for Application No. PCT/JP2011/051604 dated Sep. 27, 2012.
(Continued)

*Primary Examiner* — Sean Dougherty
*Assistant Examiner* — Nicholas E Kolderman
(74) *Attorney, Agent, or Firm* — Cheng Law Group, PLLC

(57) ABSTRACT

A plug that allows the plug body to be easily and reliably pierced through by a hollow bodily fluid collection needle, makes the bodily fluid collection needle difficult to draw back out of the plug body owing to a resilience of a sheath after the start of bodily fluid collection, and enables easy and reliable collection of the bodily fluid. The plug 1 is a plug for closing an opening end of a bodily fluid-collecting container 14 which is to be inserted into a tubular holder 11, and includes: a plug body 2 to be fixed to the opening end of the bodily fluid-collecting container 14; and a cover member 3 sheathed on the plug body 2 to cover an outer surface of the plug body 2, wherein the cover member 3 includes a side part 3c covering the outer surface of the plug body 2, and an outer surface of the side part 3c is provided with a protrusion 3k which protrudes radially outward of the side part 3c of the cover member 3 to come into contact with and give frictional
(Continued)

resistance to an inner wall of the holder 11 upon insertion into the holder 11.

13 Claims, 11 Drawing Sheets

(51) Int. Cl.
*A61J 1/14* (2006.01)
*B65D 51/00* (2006.01)
*A61B 5/154* (2006.01)
*A61J 1/20* (2006.01)

(52) U.S. Cl.
CPC .. *A61B 5/150259* (2013.01); *A61B 5/150351* (2013.01); *A61B 5/150389* (2013.01); *A61B 5/150473* (2013.01); *A61B 5/150572* (2013.01); *A61B 5/150732* (2013.01); *B65D 51/002* (2013.01); *A61J 1/2096* (2013.01)

(56) References Cited

U.S. PATENT DOCUMENTS

| | | | | |
|---|---|---|---|---|
| 4,893,636 A | * | 1/1990 | Cook et al. | 600/577 |
| 5,085,332 A | * | 2/1992 | Gettig et al. | 215/249 |
| 5,303,835 A | * | 4/1994 | Haber et al. | 215/247 |
| 5,755,701 A | * | 5/1998 | Sarstedt | 604/264 |
| 5,890,610 A | | 4/1999 | Jansen et al. | |
| 6,277,331 B1 | * | 8/2001 | Konrad | 422/547 |
| 6,391,014 B1 | * | 5/2002 | Silverman | 604/415 |
| 6,602,206 B1 | | 8/2003 | Niermann et al. | |

FOREIGN PATENT DOCUMENTS

| | | |
|---|---|---|
| EP | 1 077 086 A2 | 2/2001 |
| JP | 62-166852 U | 10/1987 |
| JP | 10-5311 A | 1/1998 |
| JP | 10-99410 A | 4/1998 |
| JP | 10216108 A * | 8/1998 |
| JP | 2000-24106 A | 1/2000 |
| JP | 2001-145685 A | 5/2001 |
| TW | 381973 | 2/2000 |

OTHER PUBLICATIONS

The First Office Action for Application No. 201180007527.1 from The State Intellectual Property Office of the People's Republic of China dated Dec. 10, 2013.
International Search Report for the Application No. PCT/JP2011/051604 dated Mar. 8, 2011.
The Third Office Action for the Application No. 201180007527.1 from The State Intellectual Property Office of the People's Republic of China dated Apr. 17, 2015.
Supplementary European Search Report for the Application No. EP 11 73 7093 dated Apr. 11, 2014.
Office Action for the Application No. 11 737 093.2 from European Patent Office dated Jan. 26, 2016.

* cited by examiner

[FIG. 1]
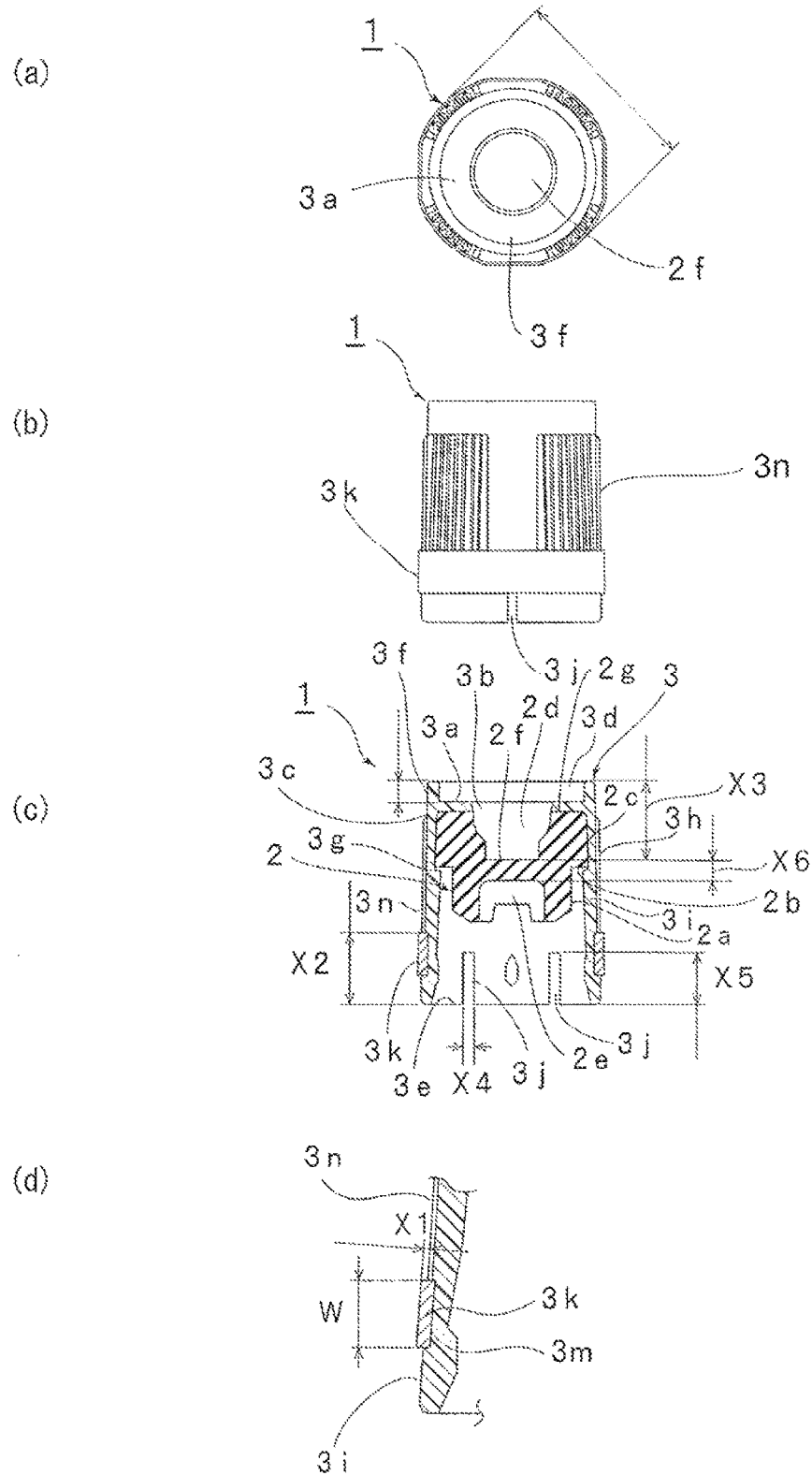

[FIG. 2]
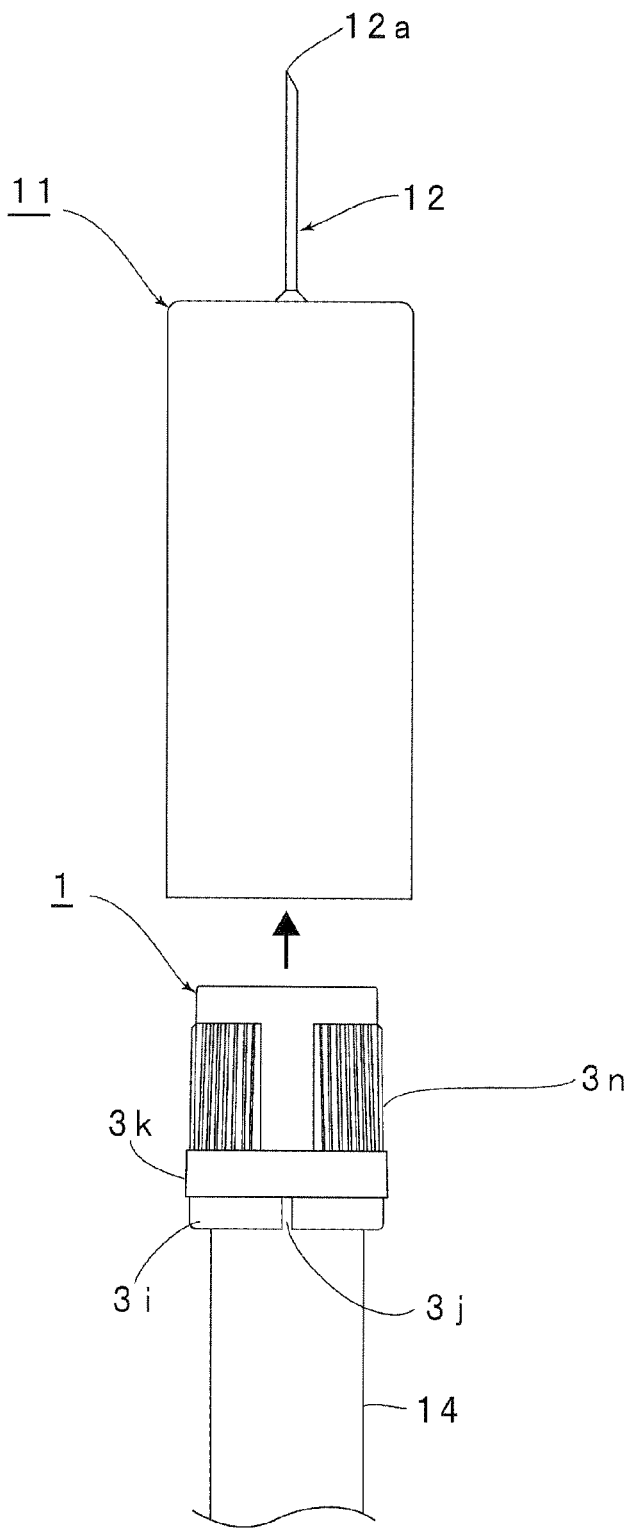

[FIG. 3]
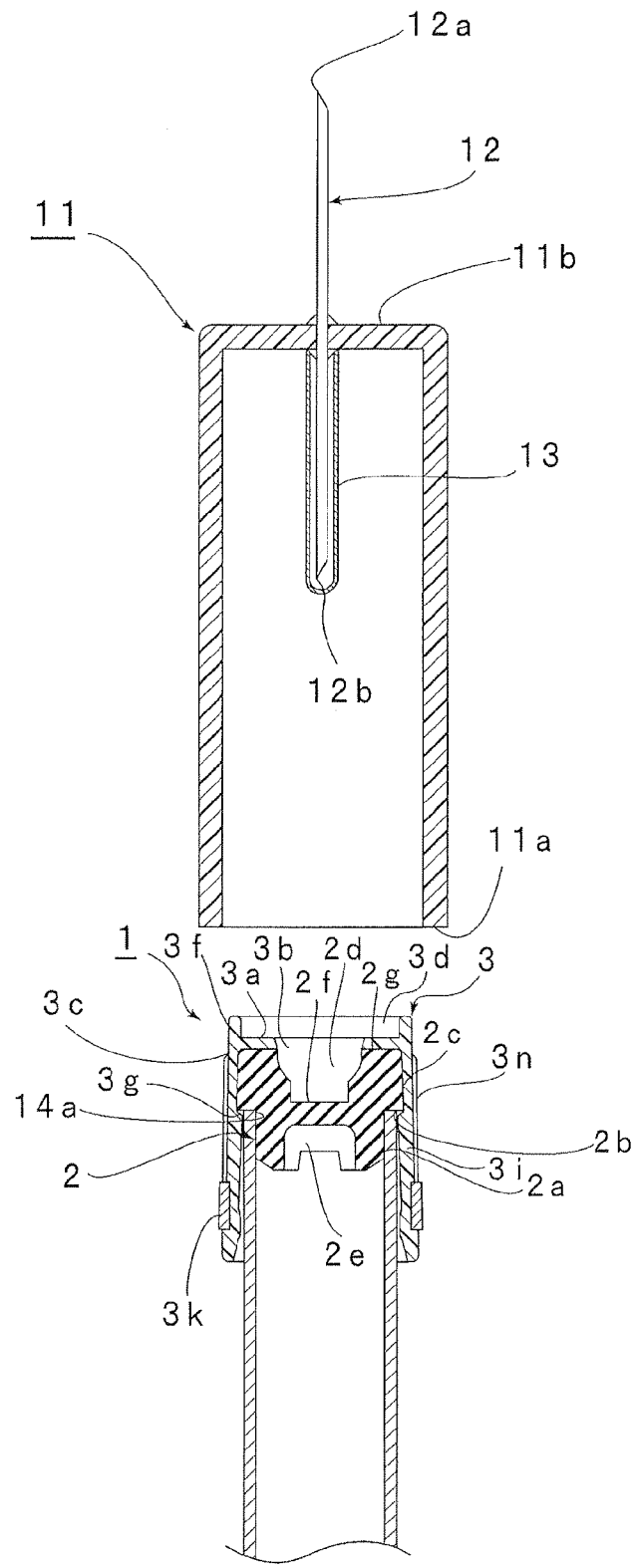

[FIG. 4]
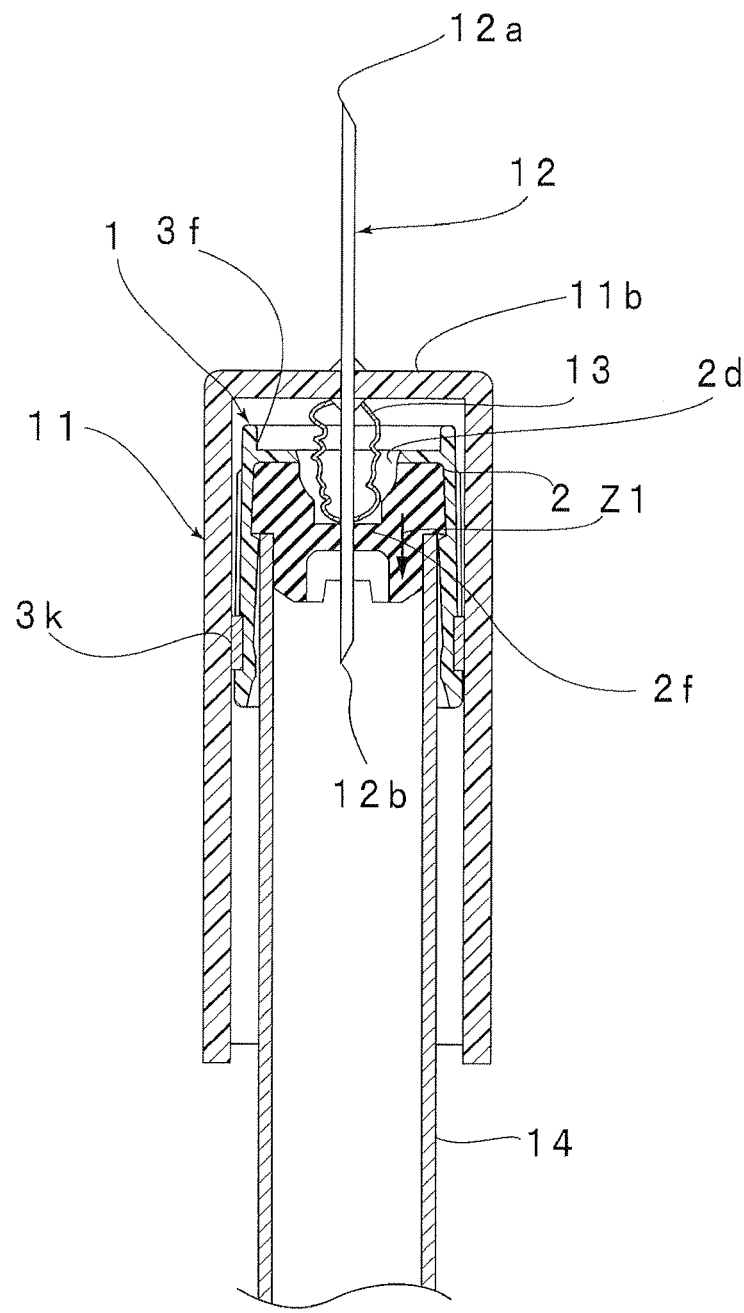

[FIG. 5]
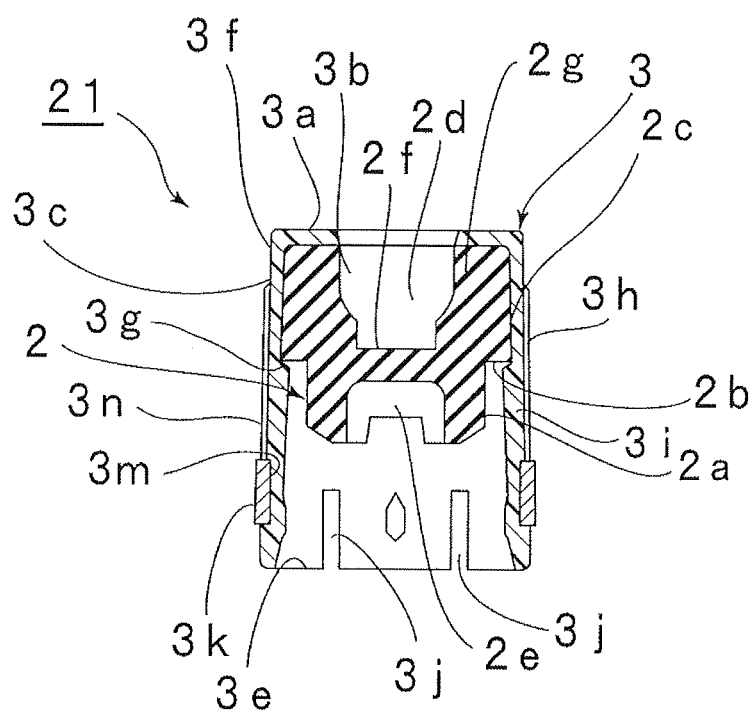

[FIG. 6]
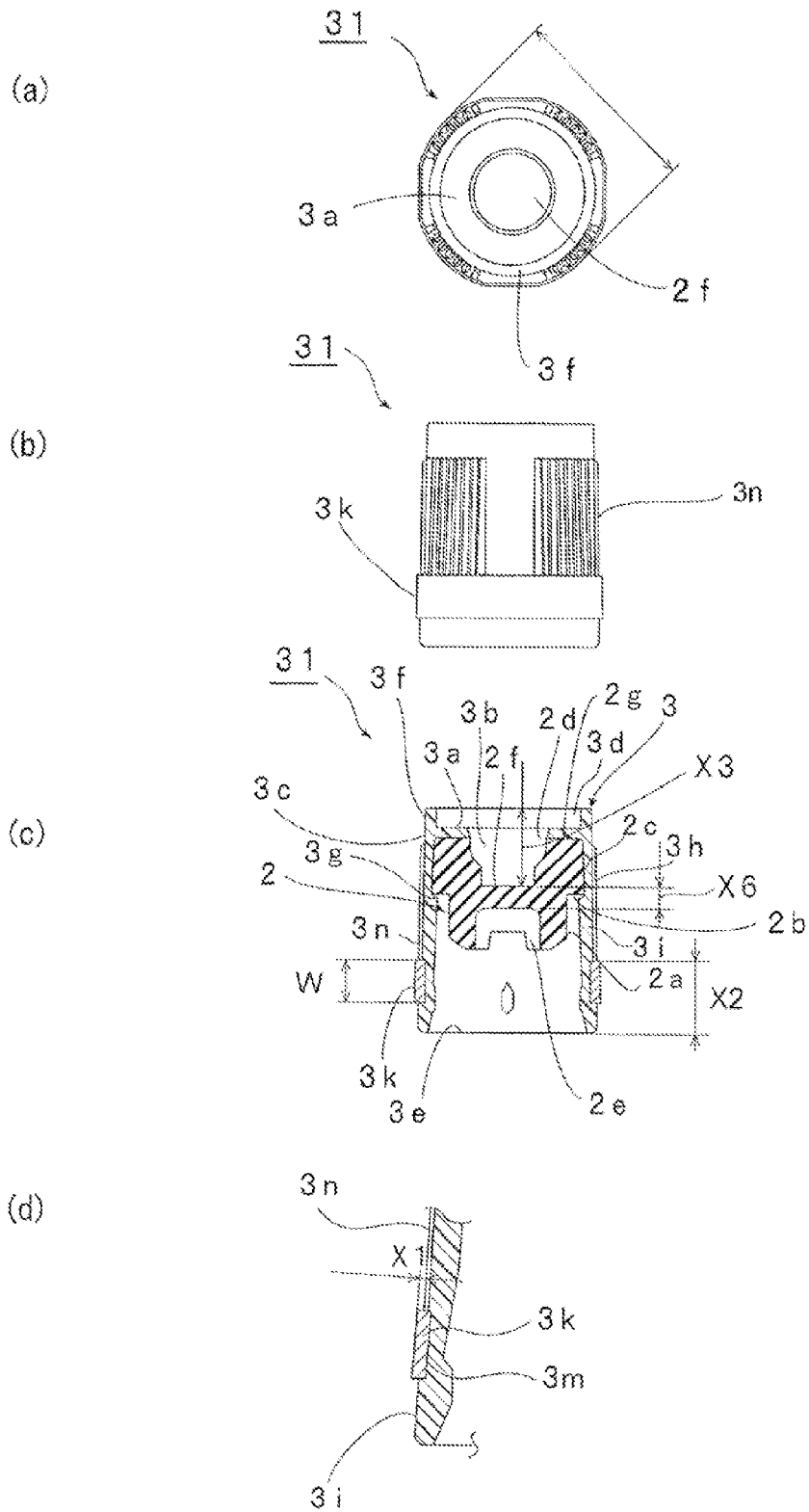

[FIG. 7]
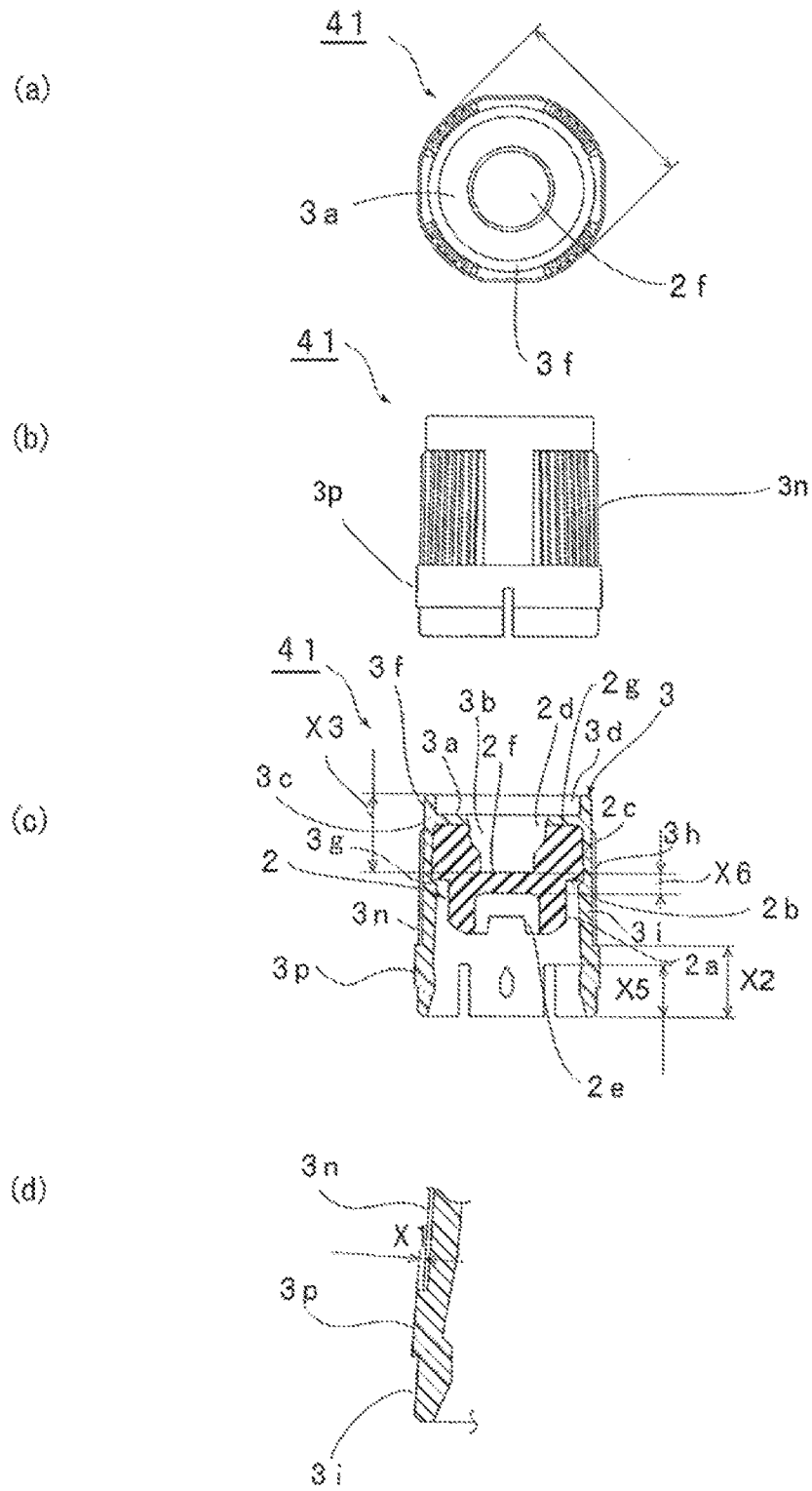

PRIOR ART
[FIG. 8]
(a) 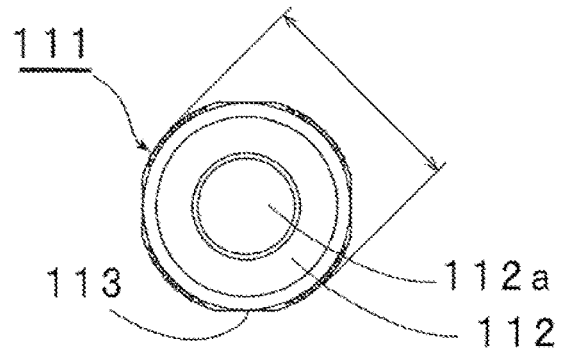
(b) 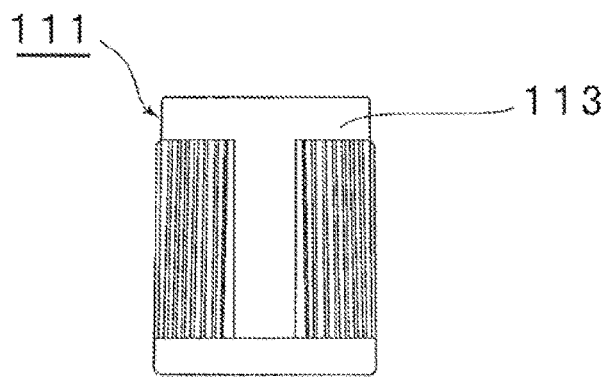
(c) 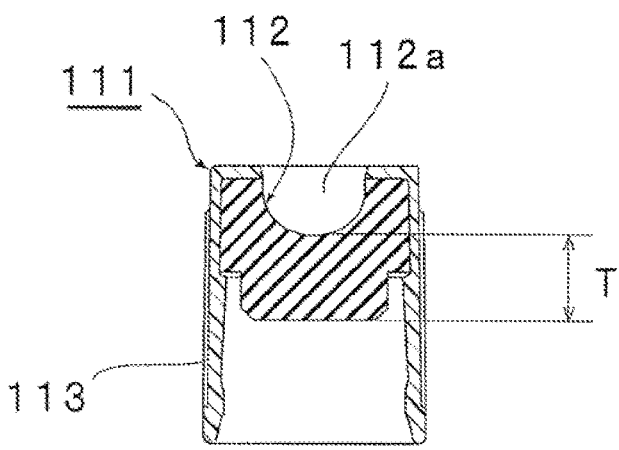

PRIOR ART
[FIG. 9]
(a)
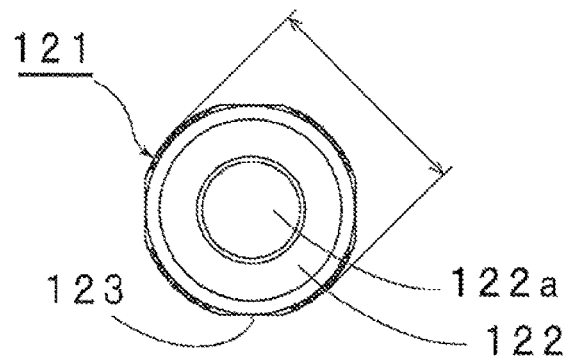
(b)
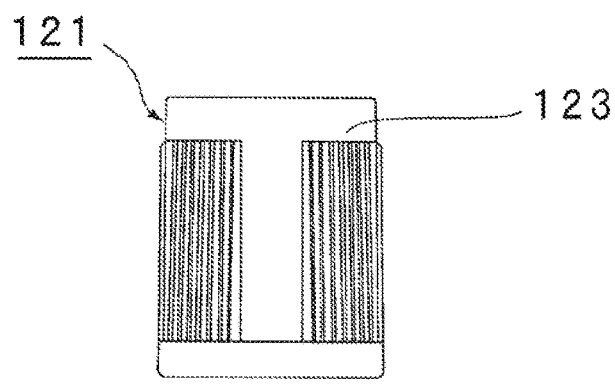
(c)
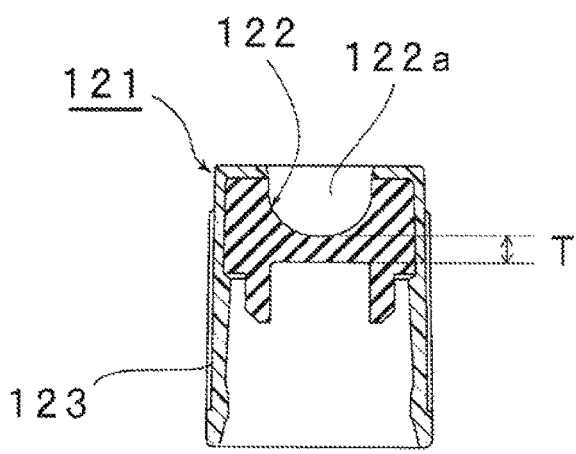

PRIOR ART
[FIG. 10]
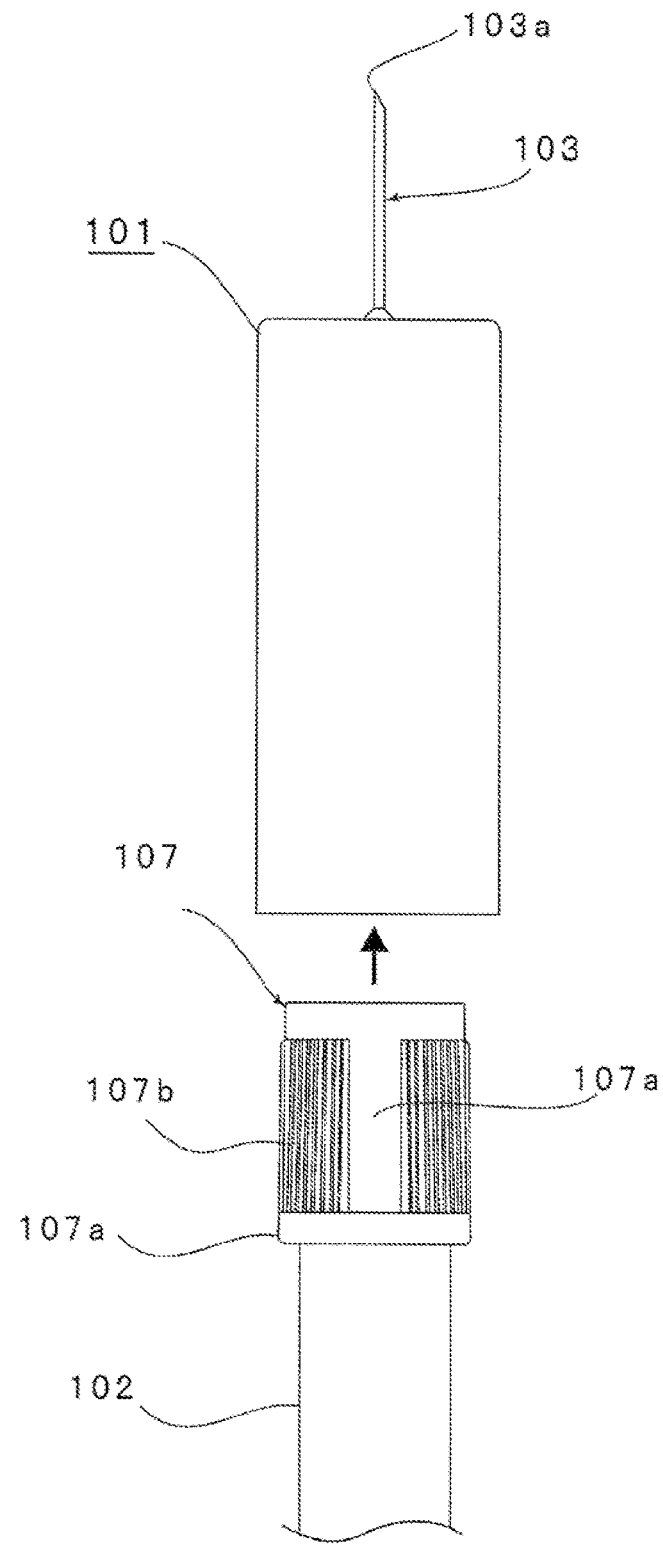

PRIOR ART
[FIG. 11]
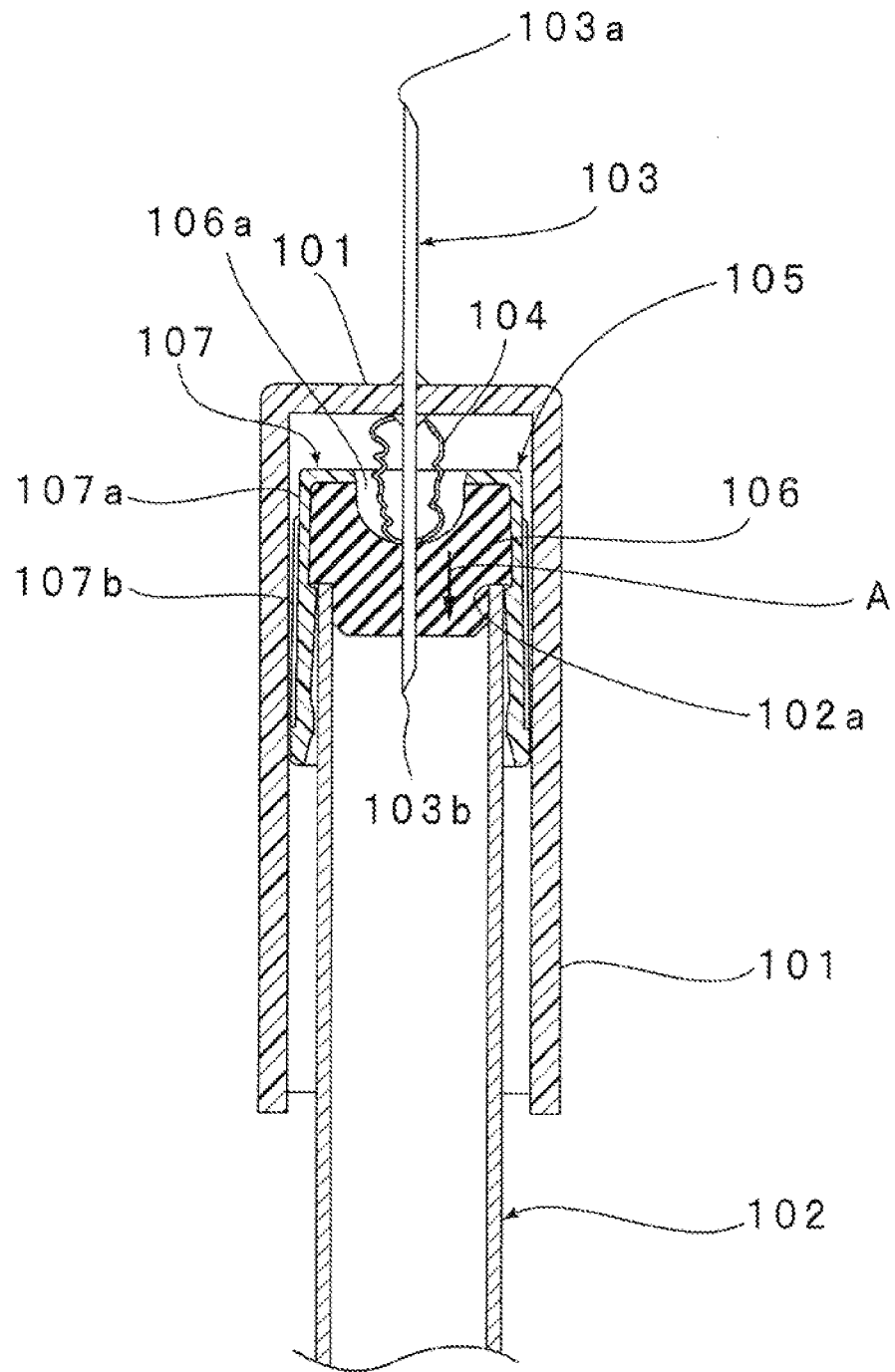

PLUG AND BODILY FLUID-COLLECTING INSTRUMENT SET

TECHNICAL FIELD

This invention relates to plugs for bodily fluid-collecting containers for collecting bodily fluid, such as blood, and more particularly relates to a plug for closing the opening of a bodily fluid-collecting container which is to be inserted into a tubular holder and a bodily fluid-collecting instrument set including a bodily fluid-collecting container with the plug.

BACKGROUND ART

To collect bodily fluid, such as blood, a holder having a hollow bodily fluid collection needle fixed thereto has heretofore been widely used. Patent Literature 1 below discloses a bodily fluid collecting method using a holder of this kind. This bodily fluid collecting method will be described with reference to FIGS. 10 and 11.

First, as shown in FIG. 10, a tubular holder 101 and a bodily fluid-collecting container 102 are prepared. As shown in a cross-sectional view in FIG. 11, a hollow bodily fluid collection needle 103 is fixed to the holder 101 to penetrate the upper end surface of the holder 101. The bodily fluid collection needle 103 has needle tips at both ends. The needle tip 103a at one end is located outside the holder 101, while the needle tip 103b at the other end extends in the interior of the holder 101. Furthermore, a sheath 104 made of an elastic material, such as rubber, is provided to envelop the portion of the bodily fluid collection needle 103 located in the interior of the holder 101. FIG. 11 shows a state that the sheath 104 is compressed so that the needle tip 103b is exposed out of the sheath 104. Before use, the sheath 104 envelops the needle tip 103b.

On the other hand, to seal an opening 102a at the upper end of the bodily fluid-collecting container 102, a plug 105 is fixed to the bodily fluid-collecting container 102.

The plug 105 includes a plug body 106 made of rubber and a cover member 107 attached to the plug body 106 to cover the outer surface of the plug body 106. A lower end portion of the plug body 106 is press-fitted into the bodily fluid-collecting container 102 to hermetically seal the opening 102a. The top surface of the plug body 106 is provided in the center with a recess 106a. The thickness of a portion of the plug body 106 provided with the recess 106a is made smaller than that of the other portion thereof. This portion having a relatively small thickness serves as a pierceable portion to be pierced through by the bodily fluid collection needle 103. Furthermore, the outer surface of a side part 107a of the cover member 107 is provided with a plurality of vertically extending ribs 107b. The ribs 107b are formed for the purpose of improving the handleability of the bodily fluid-collecting container, such as ease of removal of the plug 105 from the bodily fluid-collecting container 102 after bodily fluid collection and prevention of unexpected rolling of the bodily fluid-collecting container.

In collecting bodily fluid, e.g., in collecting blood in a bodily fluid-collecting container which is a vacuum blood collection tube, the needle tip 103a at one end of the bodily fluid collection needle 103 is inserted into a blood vessel. The blood is thus introduced into the bodily fluid collection needle, but at this point of time the blood introduced into the bodily fluid collection needle 103 never leaks out because the sheath 104 envelops the needle tip 103b. In this state, as shown in FIG. 11, the bodily fluid-collecting container 102 having the plug 105 fixed thereto is inserted into the holder 101. While in this state the bodily fluid-collecting container 102 is continued to be inserted, the needle tip 103b pierces through the pierceable portion as shown in FIG. 11. Since the interior of the bodily fluid-collecting container 102 is reduced in pressure, the blood is drawn through the bodily fluid collection needle 103 into the bodily fluid-collecting container 102.

CITATION LIST

Patent Literature

Patent Literature 1: JP-A-2001-145685

SUMMARY OF INVENTION

Technical Problem

When the bodily fluid-collecting container 102 is inserted into the holder 101 to collect the blood, the sheath 104 is compressed by the plug body 106 as shown in FIG. 11. Therefore, owing to a resilience of the sheath 104 made of an elastic material, a force in the direction indicated by the arrow A is applied to the plug body 106. If the needle tip 103b has failed to pierce through the plug body 106 or has been drawn back out of the plug body 106, the blood collection will be interrupted as it is incomplete. Therefore, the blood collecting personnel will have to apply a force to restrict the backward movement of the bodily fluid-collecting container 102 so that the bodily fluid-collecting container 102 will not be pushed back by a resilience of the sheath 104. Hence, a large burden will be imposed on the blood collecting personnel.

To reduce the burden as described above on the blood collecting personnel, the bodily fluid-collecting container 102 has conventionally been prevented from backward movement by increasing the frictional resistance between the plug body 106 and the bodily fluid collection needle 103.

However, in order to increase the frictional resistance between the bodily fluid collection needle 103 and the plug body 106, the thickness of the pierceable portion of the plug body 106 must be increased to a certain extent. As a result, the resistance of the pierceable portion upon initial piercing with the bodily fluid collection needle 103 will also be increased. This increases the burden on the blood collecting personnel for inserting the bodily fluid-collecting container 102 into the holder 101 and allowing the plug body 106 to be reliably pierced through by the bodily fluid collection needle 103. In addition, in the course of insertion of the bodily fluid-collecting container 102 into the holder 101, the bodily fluid collection needle 103 will meet with significant resistance while penetrating the pierceable portion of the plug body 106 and the resistance will sharply decrease after it penetrates through the pierceable portion. Therefore, the holder 101 is likely to be wobbled during blood collection. This makes it very difficult to stably and reliably collect bodily fluid, such as blood.

An object of the present invention is to provide a plug that can eliminate the above-mentioned disadvantages in the conventional technique, allows the plug body to be easily and reliably pierced through by a hollow bodily fluid collection needle in collecting bodily fluid, such as blood, makes the bodily fluid collection needle difficult to draw back out of the plug body owing to a resilience of the sheath after the start of bodily fluid collection, and enables easy and reliable collection of the bodily fluid, and a bodily fluid-collecting instrument set including a bodily fluid-collecting container with the plug.

Solution to Problem

A plug according to the present invention is a plug for closing, by being fitted to an opening of a tubular bodily fluid-collecting container which is to be inserted into a tubular holder, the opening, and the plug includes: a plug body to be fixed to the opening of the bodily fluid-collecting container; and a cover member sheathed on the plug body to cover an outer surface of the plug body. The cover member includes a side part covering at least the outer surface of the plug body. The side part is provided with a protrusion which protrudes radially outward of the side part of the cover member to come into contact with and give frictional resistance to an inner wall of the holder upon insertion into the holder and constitutes a maximum outside diameter portion to be pressed against the inside of the holder.

In a particular aspect of the plug according to the present invention, the side part of the cover member is provided with a plurality of slits extending to the lower end of the side part.

Furthermore, in a particular aspect of the plug according to the present invention, the protrusion is formed of an annular strip extending circumferentially on the side part of the cover member.

In a further particular aspect of the plug according to the present invention, the maximum outside diameter of the strip in a radial direction of the side part of the cover member is 17.0 to 18.5 mm.

In still another particular aspect of the plug according to the present invention, the protrusion is provided at a position spaced above the lower end of the side part of the cover member.

In still another particular aspect of the plug according to the present invention, the protrusion is provided at a position within 8 mm from the lower end of the side part of the cover member, and the protrusion thickness of the protrusion from the side part of the cover member is 0.25 to 1.5 mm.

In still another particular aspect of the plug according to the present invention, the protrusion has a vertical length of 1 to 8 mm.

In still another particular aspect of the plug according to the present invention, the protrusion is made of a material different from the cover member and fixed to the side part of the cover member.

In still another particular aspect of the plug according to the present invention, the protrusion is made of the same material as the cover member, and the protrusion and the cover member are formed by integral molding.

In still another particular aspect of the plug according to the present invention, the plug body is made of an elastic material capable of press fit into the opening of the bodily fluid-collecting container and includes a pierceable portion through which a bodily fluid collection needle is to be pierced, and the thickness of the pierceable portion is 1 mm to 4 mm.

In still another particular aspect of the plug according to the present invention, the plug body is made of an elastic material capable of press fit into the opening of the bodily fluid-collecting container and includes a pierceable portion through which a bodily fluid collection needle is to be pierced, and the pierceable portion is formed by providing a recess in a top surface of the plug body so that the pierceable portion has a relatively small thickness compared to a portion surrounding the pierceable portion.

In still another particular aspect of the plug according to the present invention, the depth of the recess is 4 mm to 8 mm.

A bodily fluid-collecting container according to the present invention has an opening at a top end thereof and is equipped at the opening with the plug configured in accordance with the present invention.

A bodily fluid-collecting instrument set according to the present invention includes: a holder including a tubular holder body having an opening at a lower end thereof and closed at an upper end thereof, a bodily fluid collection needle fixed to the holder body to penetrate the upper end of the holder body and extending at one end to the outside of the holder body and at the other end to the interior of the holder, and a sheath made of an elastic material and attached to the holder body or the bodily fluid collection needle to envelop a portion of the bodily fluid collection needle close to the other end thereof; a bodily fluid-collecting container configured to be capable of being inserted into the holder through the opening at the lower end and having an opening at an upper end thereof; and the plug configured in accordance with the present invention and fixed to the opening of the bodily fluid-collecting container.

Advantageous Effects of Invention

In the present invention, since the outer surface of the side part of the cover member is provided with a radially outwardly protruding protrusion, the frictional resistance between the inner wall of the holder and the plug can be increased. Therefore, it can be prevented that the bodily fluid collection needle is drawn back out of the plug body by a resilience of the sheath.

In addition, since the provision of the protrusion increases the above frictional resistance, the thickness of the pierceable portion of the plug body can be reduced, whereby the resistance of the pierceable portion upon initial piercing with the bodily fluid collection needle 103 can be reduced. Therefore, bodily fluid collection can be easily and reliably conducted.

BRIEF DESCRIPTION OF DRAWINGS

FIGS. 1(a) to 1(d) are a plan view of a plug according to one embodiment of the present invention, a front view thereof, a front cross-sectional view thereof, and a partly cutaway front cross-sectional view thereof in which an essential part is shown enlarged.

FIG. 2 is a front view showing the step of inserting into a holder a bodily fluid-collecting container provided with the plug according to the one embodiment of the present invention.

FIG. 3 is a front cross-sectional view showing the step of inserting into the holder the bodily fluid-collecting container provided with the plug according to the one embodiment of the present invention.

FIG. 4 is a front cross-sectional view showing the step of inserting into the holder the bodily fluid-collecting container provided with the plug according to the one embodiment of the present invention and collecting bodily fluid.

FIG. 5 is a front cross-sectional view for illustrating a modification of the plug according to the one embodiment of the present invention.

FIGS. 6(a) to 6(d) are a plan view of a plug according to a second embodiment of the present invention, a front view thereof, a front cross-sectional view thereof, and a partly cutaway front cross-sectional view thereof in which an essential part is shown enlarged.

FIGS. 7(a) to 7(d) are a plan view of a plug according to a third embodiment of the present invention, a front view thereof, a front cross-sectional view thereof, and a partly cutaway front cross-sectional view thereof in which an essential part is shown enlarged.

FIGS. 8(a) to 8(c) are a plan view, a front view, and a front cross-sectional view of a plug of Comparative Example 1 prepared for comparison.

FIGS. 9(a) to 9(c) are a plan view, a front view, and a front cross-sectional view of a plug of Comparative Example 2 prepared for comparison.

FIG. 10 is a front view for illustrating the step of inserting a conventional bodily fluid-collecting container into a holder and collecting bodily fluid.

FIG. 11 is a front cross-sectional view for illustrating the step of inserting the bodily fluid-collecting container provided with a conventional plug into the holder and collecting bodily fluid.

DESCRIPTION OF EMBODIMENTS

Hereinafter, the present invention will become apparent by explaining specific embodiments of the present invention with reference to the drawings.

FIGS. 1(a) to 1(d) are a plan view of a plug according to a first embodiment of the present invention, a front view thereof, a front cross-sectional view thereof, and a partly cutaway front cross-sectional view thereof in which an essential part is shown enlarged. Furthermore, FIG. 2 is a front view showing the step of inserting into a holder a bodily fluid-collecting container provided with the plug according to the first embodiment of the present invention.

The plug 1 includes a plug body 2 and a cover member 3. The plug body 2 serves to close the opening of a bodily fluid-collecting container. The plug body 2 includes a press-fit part 2a to be press fitted into the opening of the bodily fluid-collecting container, and a grip part 2c continued to the press-fit part 2a via a shoulder 2b extending at the upper end of the press-fit part 2a in the horizontally outward direction from the outer peripheral edge of the press-fit part 2a. In this embodiment, since the planar shape of the opening of the bodily fluid-collecting container 14 to be fitted with the plug 1 is circular, the outer periphery of the press-fit part 2a has a cylindrical shape. The outer periphery of the grip part 2c also has a cylindrical shape. However, the press-fit part 2a and the grip part 2c may have any shape other than the cylindrical outer periphery.

The outside diameter of the press-fit part 2a is made slightly larger than the diameter of the opening at the upper end of the bodily fluid-collecting container 14 to be applied to it so that it can hermetically seal the opening at the upper end of the bodily fluid-collecting container. The outside diameter of the grip part 2c is made larger than the outside diameter of the press-fit part 2a, so that the above shoulder 2b is formed.

The grip part 2c has a recess 2d in the center. The grip part 2c has an annular shape to surround the recess 2d. Furthermore, a portion of the press-fit part 2a located below the recess 2d is formed into a recess 2e opening downward. Since the recess 2d and the recess 2e are provided, the thickness of a portion of the plug body intermediate the recesses 2d and 2e opposed to each other is made smaller than that of the surrounding portion. This portion having a relatively small thickness constitutes a pierceable portion 2f.

Since the thickness of the pierceable portion 2f is small as described above, the pierceable portion can be easily and reliably pierced through by a bodily fluid collection needle as will be described later.

The planar shape of the pierceable portion 2f is circular in this embodiment, although not specifically limited to such.

The plug body 2 is preferably made of an elastic material having resiliency because the plug body 2 is fixed to the bodily fluid-collecting container 14 to hermetically seal it. An example of such an elastic material is synthetic rubber or thermoplastic elastomer.

The cover member 3 includes an annular head plate 3a provided to be capable of contact with the top surface 2g of the plug body 2. An opening 3b in the center of the head plate 3a is continued to the recess 2d.

The outer peripheral edge of the head plate 3a is continued to a side part 3c. The side part 3c is formed of a cylindrical member having a first opening 3d at the upper end and a second opening 3e at the lower end. Note that in this embodiment, compared to the inside diameters of portions thereof close to the first opening 3d, the inside diameters of portions thereof close to the second opening 3e located below the first opening 3d are made relatively large. Therefore, the cover member 3 is formed so that the opening diameter gradually increases from the upper portion toward the lower portion.

Meanwhile, in this embodiment, the side part 3c extends upward above the head plate 3a and this portion thereof upper than the head plate 3a constitutes an annular sidewall 3f. Furthermore, the inner surface of the side part 3c has a shoulder 3g formed in the direction intersecting with the direction of vertical extension of the inner wall of the side part 3c. In the portion of the side part 3c lower than the portion thereof provided with the shoulder 3g, the inside diameter of the side part 3c is made smaller than the outside diameter at the lower end of the grip part 2c of the plug body 2. Therefore, the shoulder 3g prevents the plug body 2 inserted in the cover member 3 from dropping down.

Preferably, the distance between the under surface of the head plate 3a and the shoulder 3g is made equal to or slightly smaller than the vertical dimension of the grip part 2c of the plug body 2. Thus, the plug body 2 can be press-fitted between the head plate 3a and the shoulder 3g and the fitted position can be reliably fixed.

A portion 3h of the side part 3c lower than the annular sidewall 3f and upper than the shoulder 3g is brought into close contact with the outer periphery of the grip part 2c of the plug body 2.

Therefore, in this embodiment, the inner surface of the head plate 3a and the inner surface of the portion 3h come into close contact with the outer surface of the grip part 2c of the plug body 2.

The side part 3c has a skirt 3i continued downward from the portion 3h. The skirt 3i will be located outside of the outer periphery of the bodily fluid-collecting container, as will be described later.

The lower end of the skirt 3i forms the second opening 3e. Furthermore, the skirt 3i is provided with a plurality of slits 3j extending upward from the lower end thereof. The upper ends of the slits 3j are located below the bottom end of the press-fit part 2a of the plug body 2.

Because of the provision of the plurality of slits 3j, the skirt 3i is configured to be easily deformable when receiving an external force in the radial direction. Thus, when inserted into a holder, the skirt 3i comes into contact with the inner wall of the holder to easily deform in the direction of the tube center and gives moderate frictional resistance to the inner wall of the holder. At the same time, owing to the resilience of the deformed portion, a force in the direction outward from the tube center is applied to the holder, so that the plug 1 can be held with a moderate force against the holder. This enables the accommodation of differences in inside diameter between commercially available holders made by different manufacturers, easily prevents kickback regardless of the type of holder, and facilitates the insertion and removal of the blood collection tube into and from the holder.

Furthermore, the skirt 3i is provided at the outer surface with a strip 3k serving as a protrusion in the present invention. The protrusion 3k constitutes a maximum outside diameter portion of the plug 1. This maximum outside diameter portion is made with such a size that when it is inserted into a holder, it will be pressed against and give frictional resistance to the inner wall of the holder. In this embodiment, the strip 3k is made of a material different from the cover member 3. The strip 3k is an annular strip extending circumferentially on the side part 3c of the cover member 3. However, the protrusion in the present invention may not be of an annular form extending circumferentially on the side part 3c of the cover member 3. Specifically, a plurality of protrusions may be provided along the circumferential direction.

The outer surface of the strip 3k serving as the protrusion protrudes radially outward beyond the outer surface of the side part 3c. The maximum outside diameter portion of this strip 3k constitutes the maximum outside diameter portion of the side part 3c. In other words, the diameter of the maximum outside diameter portion of the strip 3k is made larger than that of the maximum outside diameter portion of the cover member 3 formed of a separate piece from the strip 3k. Furthermore, the maximum outside diameter portion of the strip 3k is made with such a size that when it is inserted into a below-mentioned holder, it will come into contact with and give frictional resistance to the inner wall of the holder. Thus, the frictional resistance between the inner wall of the holder and the plug 1 can be increased to prevent the plug body 2 from slipping out of the needle upon collection of bodily fluid.

The material forming the strip 3k is preferably a material that can increase the frictional resistance. Examples of such a material include elastic materials, such as rubber and thermoplastic elastomer; relatively soft polyolefins, such as low-density polyethylene and linear low-density polyethylene; and mixtures of low-density polyethylene, linear low-density polyethylene or the like and high-density polyethylene.

The cover member 3 formed of a separate piece from the strip 3k is preferably made of synthetic resin because of ease of molding. Examples of such synthetic resin include polyolefins, such as polyethylene and polypropylene.

As shown in FIG. 1(d), a portion of the side part 3c provided with the strip 3k has an annular groove 3m formed therein to correspond to the shape of the strip 3k. A portion of the strip 3k is set in the annular groove 3m, so that the vertical position of the strip 3k is fixed. Therefore, the amount X1 of protrusion of the strip 3k from the outer surface of the side part 3c is smaller than the thickness of the strip 3k. However, such an annular groove 3m may not necessarily be provided. Specifically, the strip 3k may be fixed, by adhesion or otherwise, to the outer periphery of the side part 3c.

Furthermore, in this embodiment, the lower end of the strip 3k is located above the lower end of the side part 3c.

A feature of the plug 1 of this embodiment is that the protrusion formed of the strip 3k is provided on the outer surface of the side part 3c of the cover member 3. Thus, as described previously, when a bodily fluid-collecting container is inserted into a holder, the frictional resistance between the plug 1 and the inner wall of the holder can be increased. Therefore, it is preferred that the dimensions of the strip 3k forming the protrusion and the dimensions of the remaining parts of the plug 1 should be selected depending upon the dimensions of a holder used. Hereinafter, a holder taken as an example and widely used in combination with a blood collecting container or the like has an inside diameter of 16 mm to 18 mm, and the dimension of the space in the holder in the height direction is 44 mm to 49 mm. This common holder is made of synthetic resin, such as polypropylene.

Therefore, a description will be given below of preferred dimensions of the plug when used in combination with the above holder.

In the plug 1, the maximum outside diameter of the strip 3k is preferably within the range of 17.0 to 18.5 mm. The inside diameter of a holder commonly used in combination with a blood collecting container or the like is generally 16 mm to 18 mm, as described above. Therefore, when the maximum outside diameter of the strip 3k is within the range of 17.0 to 18.5 mm, the magnitude of frictional resistance between the holder inner wall and the strip 3k can be a moderate value. If the maximum outside diameter thereof is below 17.0 mm, the magnitude of the frictional resistance will be small, which may make it difficult to reliably prevent a bodily fluid collection needle fixed to a holder from drawing back out of the plug 1. If the maximum outside diameter thereof is above 18.5 mm, this may make it difficult to insert the plug 1.

Furthermore, in the plug 1, the distance X2 between the upper end of the strip 3k and the lower end of the side part 3c is preferably within 8 mm. An additional structure for the purpose of improving handleability is often formed at the upper end of the interior of the holder and in the vicinity of a point at which a bodily fluid collection needle is fitted in the holder. However, provided that the distance X2 is within 8 mm, the plug, upon insertion into a holder, can exhibit its effect without being affected by the internal configuration of the holder end in the vicinity of the point at which the needle is fitted in the holder. The width of the strip 3k, i.e., the width W in FIG. 1(d), is preferably within the range of 1 to 8 mm. If the width is below 1 mm, the effect of increasing the frictional resistance may not be able to be sufficiently achieved. If the width is above 8 mm, the frictional resistance may become too high.

The above amount X1 of protrusion is preferably 0.25 mm to 1.5 mm. Within this range of amounts of protrusion, the frictional resistance can have a moderate value. If the amount of protrusion is below 0.25 mm, the effect of increasing the frictional resistance may not be able to be sufficiently achieved. If the amount of protrusion is above 1.5 mm, the frictional resistance may become too high, which may make it difficult to insert the plug into and remove it from the holder.

In this embodiment, the strip 3k is made of vulcanized rubber or thermoplastic elastomer in the range of A10 to A99 Shore hardness measured in accordance with JIS K7215. The use of vulcanized rubber or thermoplastic elastomer in this hardness range is desirable because it can give moderate frictional resistance against the holder inner wall.

The total dimension X3 of the height of the annular sidewall 3f above the head plate 3a and the depth of the recess 2d provided in the plug body 2 is preferably 4 mm to 8 mm. When the dimension X3 is within the range of 4 mm to 8 mm, a space with a moderate volume can be formed above the pierceable portion 2f. Thus, a space for accommodating a below-mentioned compressed sheath with ease can be reserved.

The plurality of slits 3j are provided in order to increase the flexibility toward an external force applied to the skirt 3i in the radial direction as described previously, and the width X4 of each slit is preferably 1 to 3 mm. With the use of slits having a width in this range, the deformability of the skirt 3i can be increased. Furthermore, the depth X5 of each slit 3j, i.e., the length X5 from the lower end of the cover member 3 to the upper end of the slit 3j, is preferably within 8 mm. If X5 is above 8 mm, the vertical dimension of the cover member 3 will be large, so that the plug 1 will be of large size. When X5 is within 8 mm, the effect of increasing the flexibility can be sufficiently achieved and the plug 1 can be downsized.

When a bodily fluid-collecting container with the plug of the present invention is laid down on something, the container will come into contact with it at, for example, the lower end of a below-mentioned portion 3i or portion 3p in FIG. 7(d). If in this case slits are provided in the manner described above, cutaway sections are formed in the periphery of the lower end of the portion 3i or portion 3p, so that rolling of the bodily fluid-collecting container can be prevented. Therefore, it can be prevented that when the bodily fluid-collecting container with the plug of the present invention is laid down on a table after the collection of bodily fluid, the container rolls and falls down from the table.

The number of the plurality of slits 3j may be any number but three or more slits are preferably provided. Thus, the flexibility can be further increased.

No particular limitation is placed on the upper limit of the number of slits so long as the total length of missing portions of the strip due to slits is 50% or less of the entire circumference of the strip throughout which, if the strip had no slit, it could come into contact with the holder inner surface. For example, when the outside diameter of the strip is selected to be 17.0 mm and the slit width is selected to be 3 mm, the number of slits is preferably eight or less. When the outside diameter of the strip is selected to be 18.5 mm and the slit width is selected to be 3 mm, the number of slits is preferably nine or less.

For example, for a bodily fluid collection needle with a needle gauge of 21 G, the thickness X6 of the pierceable portion 2f is preferably within the range of 1 mm to 4 mm. If the thickness X6 thereof is below 1 mm, this will increase the pierceability but may be likely to cause the bodily fluid collection needle to draw back out thereof.

If X6 is above 4 mm, the piercing resistance will be too high, which may make the piercing work difficult.

On the side part 3c, a plurality of vertically extending ribs 3n are formed above the strip 3k. The ribs 3n enables the plug 1 to be easily removed from the bodily fluid-collecting container when the plug 1 is gripped with the hand.

Next, a description will be given of a method of use and effects of the plug 1 with reference to FIGS. 2 to 4. In collecting bodily fluid, a tubular holder 11 as shown in FIGS. 2 and 3 is prepared. Note that the tubular holder 11 shown in FIGS. 2 and 3 is a schematic view of a common holder conventionally used, such as in a blood collecting operation using a vacuum blood collection needle. The holder 11 is made of synthetic resin and has an approximately cylindrical shape. The holder 11 has an opening 11a formed at the lower end. The upper end of the holder 11 is closed by a head plate 11b. A bodily fluid collection needle 12 is provided through and fixed to the head plate 11b. The bodily fluid collection needle 12 is made of metal, such as stainless steel. The bodily fluid collection needle 12 is a hollow needle which generally has a linear shape and the inside of which is hollow. The bodily fluid collection needle 12 has a first needle tip 12a at a first end and a second needle tip 12b at the opposite second end. The first needle tip 12a is located outside the holder 11, while the second needle tip 12b is located in the interior of the holder 11.

In the interior of the holder 11, a sheath 13 made of an elastic material, such as rubber, is provided to envelop the bodily fluid collection needle 12. The sheath 13 is fixed at the upper end to the under surface of the head plate 11b of the holder 11. Furthermore, the lower end of the sheath 13 is located below the second needle tip 12b, and the portion of the bodily fluid collection needle 12 located in the holder 11 is enveloped with the sheath 13.

In collecting bodily fluid, such as blood, the first needle tip 12a of the bodily fluid collection needle 12 fixed to the holder 11 is inserted into a blood vessel, for example. On the other hand, the plug 1 is previously fixed to the bodily fluid-collecting container 14 for collecting the bodily fluid, such as blood. Normally, a structure is prepared in which the plug 1 is previously fixed to the bodily fluid-collecting container 14 as shown in FIGS. 2 and 3. In this case, the press-fit part 2a of the plug body 2 of the plug 1 is press-fitted into the bodily fluid-collecting container 14 through the opening 14a at its top end. Thus, the interior of the bodily fluid-collecting container 14 is hermetically sealed. Furthermore, in order to draw the bodily fluid using a pressure difference, the interior of the bodily fluid-collecting container 14 is reduced in pressure.

Since as described previously the shoulder 2b is formed between the press-fit part 2a and the grip part 2c, the press fit of the plug body 2 into the bodily fluid-collecting container 14 is completed by the abutment of the shoulder 2b on the top end of the bodily fluid-collecting container 14. Therefore, the plug body 2 can be reliably press-fitted into the bodily fluid-collecting container 14 and the press-fitted state can be fixed.

As shown in FIG. 3, with the press-fit part 2a press-fitted in the bodily fluid-collecting container 14, the above-mentioned skirt 3i of the cover member 3 is located to surround the outer periphery of the bodily fluid-collecting container 14. In this case, the inside diameter of the skirt 3i is made slightly larger than the outside diameter of the bodily fluid-collecting container 14, as shown in the figure. Therefore, the skirt 3i never prevents the press fit of the plug body 2 into the bodily fluid-collecting container 14.

Next, the bodily fluid-collecting container 14 is inserted into the holder 11 from the plug 1 side. As a result, as shown in FIG. 4, the second needle tip 12b of the bodily fluid collection needle 12 pierces through the pierceable portion 2f of the plug body 2 of the plug 1, so that the second needle tip 12b is located in the interior of the bodily fluid-collecting container 14. Thus, the bodily fluid, such as blood, is introduced into the interior of the bodily fluid-collecting container 14 by a pressure difference.

In the course of insertion of the bodily fluid-collecting container 14 into the holder 11, the sheath 13 first comes into contact with the plug body 2, and the needle tip 12b then comes into contact with the inner surface of the sheath 13, is then further thrust forward, and finally sticks out through the sheath 13. Therefore, the sheath 13 is left above the plug body 2. In addition, as the insertion work progresses, the sheath 13 is gradually compressed and, as shown in FIG. 4, confined in a space surrounded by the recess 2d of the plug body 2 and the annular sidewall 3f. In this case, when the sheath 13 is compressed, a resilience shown in the arrow Z1 acts on the plug body 2.

If the resilience is too large, the plug body 2 might be moved downward against the bodily fluid collection needle 12, so that the needle tip 12b might draw back out of the plug body 2.

However, since in the plug 1 of this embodiment the frictional resistance between the outer surface of the strip 3k and the inner wall of the holder 11 is increased, the plug body 2 is less likely to be moved downward. In other words, the frictional resistance can reduce the effect of the resilience. Therefore, the needle tip 12b is prevented from drawing back out of the plug body 2.

Since thus the strip 3k prevents the above draw-out, the thickness of the pierceable portion 2f of the plug 1 can be reduced. Therefore, the work of inserting the bodily fluid-collecting container 14 into the holder 11 and collecting bodily fluid can be easily and reliably conducted.

Furthermore, the plug body 2 need not have the function of preventing the draw-out of the needle tip 12b, so that the design flexibility of the material forming the plug body 2 and the shape of the plug body 2 can be increased.

Although in this embodiment the annular sidewall 3f is provided in an upper portion of the cover member 3, no annular sidewall may be provided above the head plate 3a, as in a plug 21 of a modification shown in FIG. 5.

Next, a description will be given of plugs according to second and third embodiments with reference to FIGS. 6 and 7.

FIGS. 6(a) to 6(d) are a plan view of a plug 31 according to a second embodiment of the present invention, a front view thereof, a front cross-sectional view thereof, and a front cross-sectional view thereof in which an essential part is shown enlarged.

The plug 31 of the second embodiment is the same as that of the first embodiment except that the plurality of slits 3j are not provided. Like this, the plurality of slits 3j may not necessarily be provided.

A plug 41 of the third embodiment shown in FIGS. 7(a) to 7(d) consists in that in place of the strip 3k, a protrusion 3p is provided. The protrusion 3p is made of the same material as the cover member 3 by integral molding. Like this, the protrusion in the present invention may be integrally molded from the same material as the cover member 3. In this case, the number of material types can be reduced and the production cost can be reduced.

Next, effects of the present invention will become apparent by comparison of specific examples and comparative examples. In the following examples and comparative examples, all of the plug bodies are made of butyl rubber having a Shore hardness of A50. Furthermore, all of the cover members are synthesized as synthetic resin molded articles made of polyethylene.

Example 1

The plug 1 of the first embodiment shown in FIG. 1 was prepared as Example 1. In this case, the strip 3k was formed from a styrene-based thermoplastic elastomer having a Shore hardness of A25. Furthermore, in Example 1, the amount X1 of protrusion of the strip 3k was 0.7 mm, the width W thereof was 4 mm, and the outside diameter of the maximum outside diameter portion thereof was 18 mm. The distance X2 between the upper end of the strip 3k and the lower end of the skirt 3i was 7 mm. Moreover, the dimension X3, which is the total of the height of the annular sidewall 3f and the depth of the recess 2d, was 7.5 mm. The width X4 of each slit 3j was 1 mm, and the height X5 thereof was 5 mm. The number of slits 3j was three.

The thickness of the pierceable portion 2f was 2 mm.

Example 2

The plug 31 of the second embodiment was used as Example 2. Example 2 was the same as Example 1 except that it had no slit 3j.

Example 3

The plug 41 of the third embodiment was used as Example 3. The strip was formed together with the cover member by integrally molding a resin made of a mixture of linear low-density polyethylene and high-density polyethylene. The amount X1 of protrusion of the integrally provided protrusion was 0.5 mm, the width W thereof was 4 mm, and the maximum outer diameter of a portion provided with the protrusion was 17.5 mm. The other dimensions were equal to those of Example 1. The distance from the upper end of the strip-like protrusion to the lower end of the cover member was 7 mm.

Comparative Example 1

A plug 111 shown in FIGS. 8(a) to 8(c) was prepared as Comparative Example 1. In this case, the thickness T of a pierceable portion was 6.5 mm, and the maximum outside diameter of a cover member 113 was 16.5 mm. The top surface of a plug body 112 has a 5.5 mm deep recess 112a formed therein.

Comparative Example 2

A plug 121 shown in FIGS. 9(a) to 9(c) was prepared as Comparative Example 2. In this case, the thickness T of a pierceable portion was 2 mm. The maximum outside diameter of a cover member 123 was 16.5 mm. The top surface of a plug body 122 has a 5.5 mm deep recess 122a formed therein.

(Evaluation of Examples and Comparative Examples)

Each of the plugs prepared in Examples and Comparative Examples was fitted into the top end opening of a bottomed, cylindrical bodily fluid-collecting container having a collection volume of 7 cc, and the container was then inserted into a holder 11 shown in FIG. 2 with hands. The opening diameter at the top end of the bodily fluid-collecting container is 11 mm. The dimension of the internal space of the holder 11 in the height direction is 48 mm. The dimensions of the prepared holders are as described below. Furthermore, the holder 11 is formed from a resin made of polypropylene. The holder 11 is a general-purpose product widely used for blood collection, and the like. In this case, a holder (VENOJECT II holder SD) and a bodily fluid collection needle (VENOJECT II blood collection needle S, 21 G) both manufactured by Terumo Corporation were used for examination (wherein since FIGS. 2 and 3 are schematic views, a portion of the holder at which the bodily fluid collection needle is held and other portions are different from those of an actual holder).

The opening diameter at the lower end of the holder 11 is 17 mm, the holder 11 has an approximately cylindrical shape, and the inside diameter thereof is substantially constant in the length direction. Therefore, the inside diameter of the holder 11 is equal to the above opening diameter. Furthermore, the dimension of the internal space of the holder 11 in the height direction is 48 mm. Moreover, a bodily fluid collection needle with a needle gauge of 21 G is fixed to the holder 11. The outside diameter of the bodily fluid collection needle is 0.8 mm. The length of the bodily fluid collection needle from the head plate of the holder 11 to the second needle tip is 17 mm. Moreover, the bodily fluid collection needle is made of stainless steel.

Evaluation was made of the feeling of impact when each bodily fluid-collecting container having a plug fixed thereto was inserted into the holder and, by visual observation, whether or not the bodily fluid-collecting container had drawn back out of the holder when the hand's grip on the holder was released after the piercing of the needle tip through the pierceable portion. The results are shown in Table 1 below. The meanings of the evaluation signs in Table 1 are as follows.

(Evaluation of Feeling of Impact)

Impact Upon Insertion:

circle means that the feeling of impact is small; triangle means that the feeling of impact is medium; and cross means that the feeling of impact is large.

(Evaluation of Draw-Out Upon Release of Hand's Grip)

circle means that the tube did not spontaneously move back; and cross means that the tube spontaneously moved back.

TABLE 1

| Type | Feeling of Impact | Tube Back |
|---|---|---|
| Ex. 1 | ○ | ○ |
| Ex. 2 | ○ | ○ |
| Ex. 3 | ○ | ○ |
| Comp. Ex. 1 | x | ○ |
| Comp. Ex. 2 | Δ | x |

(Measurement of Piercing Resistance)

Using the plugs, the bodily fluid-collecting containers, the holders, and the bodily fluid collection needles prepared in the above Examples 1, 2, and 3 and Comparative Example 1, measurement was made in terms of the maximum value of resistance when each bodily fluid-collecting container having the plug fixed thereto was inserted into the holder at a rate of 200 mm/min (i.e., the maximum value of piercing resistance). The results are shown in Table 2 below. The meanings of the evaluation signs in Table 2 are the same as those in Table 1.

It can be seen that Examples 1, 2, and 3 exhibit the maximum values of piercing resistance lower than Comparative Example 1 and, therefore, the burden on the personnel conducting bodily fluid collection by inserting a bodily fluid-collecting container can be reduced.

TABLE 2

| Type | Maximum Value of Piercing Resistance (kgf) |
|---|---|
| Ex. 1 | 1.0 |
| Ex. 2 | 1.2 |
| Ex. 3 | 1.0 |
| Comp. Ex. 1 | 1.5 |

REFERENCE SIGNS LIST

1 . . . Plug
2 . . . Plug body
2a . . . Press-fit part
2b . . . Shoulder
2c . . . Grip part
2d, 2e . . . Recess
2f . . . Pierceable portion
2g . . . Top surface
3 . . . Cover member
3a . . . Head plate
3c . . . Side part
3d . . . First opening
3e . . . Second opening
3f . . . Annular sidewall
3g . . . Shoulder
3h . . . Portion
3i . . . Skirt
3j . . . Slit
3k . . . Strip
3m . . . Annular groove
3n . . . Rib
3p . . . Protrusion
11 . . . Holder
11a . . . Opening
11b . . . Head plate
12 . . . Bodily fluid collection needle
12a . . . First needle tip
12b . . . Second needle tip
13 . . . Sheath
14 . . . Bodily fluid-collecting container
14a . . . Opening
21, 31, 41 . . . Plug

The invention claimed is:

1. A plug for closing, by being fitted to an opening of a tubular bodily fluid-collecting container which is to be inserted into a tubular holder, the opening, the plug comprising:
a plug body to be fixed to the opening of the bodily fluid-collecting container; and
a cover member with which the plug body is sheathed so that an outer surface of the plug body is covered,
wherein the cover member includes a side part covering at least the outer surface of the plug body, and an outer surface of the side part of the cover member is provided with a protrusion which protrudes radially outward of the side part of the cover member to come into contact with and give frictional resistance to an inner wall of the holder upon insertion into the holder and constitutes a maximum outside diameter portion to be pressed against the inside of the holder;
wherein the protrusion is formed of a strip extending circumferentially on the side part of the cover member;
wherein the strip has two planar walls that each extend from and intersect with the side part of the cover member, and an outer wall that connects the two planar walls, and more than 50% of the outer wall makes surface contact against an inner surface of the holder;
wherein a lower end of the side part of the cover member defines an opening in the plug through which a portion of the tubular bodily fluid-collecting container comprising the opening of the tubular bodily fluid-collecting container can be inserted; and
wherein the side part of the cover member is provided with a plurality of slits extending to the lower end of the side part.

2. The plug according to claim 1, wherein the maximum outside diameter of the strip in a radial direction of the side part of the cover member is 17.0 to 18.5 mm.

3. The plug according to claim 1, wherein the protrusion is provided at a position spaced apart from a plane corresponding to the lower end of the side part of the cover member.

4. The plug according to claim 1, wherein the protrusion is provided at a position within 8 mm from the lower end of the side part of the cover member, and the protrusion thickness of the protrusion from the side part of the cover member is 0.25 to 1.5 mm.

5. The plug according to claim 4, wherein the protrusion has a vertical length of 1 to 8 mm.

6. The plug according to claim 1, wherein the protrusion is made of a material different from the cover member and fixed to the side part of the cover member.

7. The plug according to claim 1, wherein the protrusion is made of the same material as the cover member, and the protrusion and the cover member are formed by integral molding.

8. The plug according to claim 1, wherein the plug body is made of an elastic material capable of press fit into the opening of the bodily fluid-collecting container and includes a pierceable portion through which a bodily fluid collection needle is to be pierced, and the thickness of the pierceable portion is 1 mm to 4 mm.

9. The plug according to claim 1, wherein the plug body is made of an elastic material capable of press fit into the opening of the bodily fluid-collecting container and includes a pierceable portion through which a bodily fluid collection needle is to be pierced, and the pierceable portion is formed by providing a recess in a top surface of the plug body so that the pierceable portion has a relatively small thickness compared to a portion surrounding the pierceable portion.

10. The plug according to claim 9, wherein the depth of the recess is 4 mm to 8 mm.

11. A bodily fluid-collecting container having an opening at a top end thereof and being equipped at the opening with the plug according to claim 1.

12. A bodily fluid-collecting instrument set comprising:
a holder including a tubular holder body having an opening at a lower end thereof and closed at an upper end thereof, a bodily fluid collection needle fixed to the holder body to penetrate the upper end of the holder body and extending at one end to the outside of the holder body and at the other end to the interior of the holder, and a sheath made of an elastic material and attached to the holder body or the bodily fluid collection needle to envelop the other end of the bodily fluid collection needle;
a bodily fluid-collecting container configured to be capable of being inserted into the holder through the opening at the lower end and having an opening at an upper end thereof; and the plug according to claim 1 and fixed to the opening of the bodily fluid-collecting container.

13. The plug according to claim 1, wherein the slits extend to an inner region of the strip.

* * * * *